United States Patent [19]
Lam et al.

[11] 4,049,669
[45] Sept. 20, 1977

[54] PROCESS FOR PREPARING 5-(ALKOXY- AND AMINOETHYL THIO)METHYLTHIAZOLE COMPOUNDS

[75] Inventors: Bing Lun Lam, Haverford; Joseph James Lewis; Robert Lee Webb, both of West Chester; George Robert Wellman, Warminster, all of Pa.

[73] Assignee: SmithKline Corporation, Philadelphia, Pa.

[21] Appl. No.: 626,812

[22] Filed: Oct. 29, 1975

[51] Int. Cl.² .......................................... C07D 277/40

[52] U.S. Cl. .......................... 260/306.8 R; 260/302 R; 260/590 D; 260/593 H; 260/599; 260/601 R

[58] Field of Search ................................ 260/306.8 R

*Primary Examiner*—Richard J. Gallagher
*Attorney, Agent, or Firm*—Janice E. Williams; William H. Edgerton; Alan D. Lourie

[57] ABSTRACT

A process for preparing 5-(alkoxy- and aminoethylthio)methylthiazole compounds via displacement of the trisubstituted phosphonium group from 5-(trisubstituted phosphonium)methylthiazole compounds is disclosed.

10 Claims, No Drawings

PROCESS FOR PREPARING 5-(ALKOXY- AND AMINOETHYL THIO)METHYLTHIAZOLE COMPOUNDS

This invention relates to a process for preparing substituted thiazole compounds which are useful intermediates in the preparation of compounds having pharmacological activity. In particular the invention relates to a process for preparing 5-(alkoxy- and aminoethylthio)-methylthiazoles via displacement of the trisubstituted phosphonium group from a 5-(trisubstituted phosphonium)methylthiazole compound which is represented as follows:

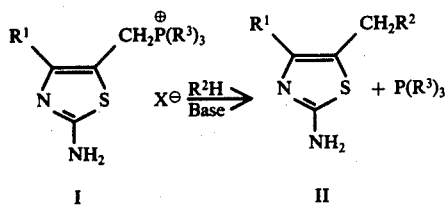

in which $R^1$ is hydrogen or lower alkyl, preferably methyl; $R^2$ is methoxy, ethoxy, n-propoxy, n-butoxy, i-butoxy, t-butoxy or $-SCH_2CH_2NH_2$, preferably methoxy or $-SCH_2CH_2NH_2$; $R^3$ is lower alkyl or, preferably, phenyl and X is halo, preferably chloro or bromo.

As used herein, the term "lower alkyl" refers to groups containing from one to four carbon atoms.

According to the above process, the displacement of a trisubstituted phosphonium group $[-P^+(R^3)_3]$ of a compound of formula I is effected by reaction of a compound of formula I with a slight excess of a nucleophile $R^{2-}$, prepared from in situ reaction of a compound of the formula $R^2H$ and a strong base. The reaction is carried out in an organic solvent, with solvents such as methanol, ethanol, propanol, butanol, acetone, acetonitrile, dimethylformamide and dimethylsulfoxide being preferred. Preferably, the reaction is carried out at a temperature ranging from about ambient temperature to the reflux temperature of the solvent used in the reaction viz. from about 25° to about 200° C., from about 50° to about 100° C. being advantageous, for from about 20 minutes to about 24 hours, advantageously from about 20 minutes to about 3 hours. Among the bases which are usable in the process of this invention are those which are capable of removing the proton from a compound of the formula $R^2H$ to form the anion $R^{2-}$ where $R^2$ is defined as above. Such bases are those having a pKa greater than 12, for example the alkali metal alkoxides such as sodium methoxide or ethoxide or the metal hydrides such as sodium hydride which are preferred.

Preferably, the reaction mixture is worked up by dilution with water and removal of the trialkyl- or triphenylphosphine by-product by filtration. Extraction of the filtrate when necessary followed by evaporation gives the compounds of formula II. It is often desirable to convert the compounds of formula II to the corresponding salts, preferably hydrochloride salts. Such salts are prepared by treating a solution of the thiazole of formula II with an acid or acid solution, for example with an ethereal or ethanolic solution of hydrochloric acid and crystallizing the salt produced from an appropriate solvent.

The 5-(trisubstituted phosphonium)-methylthiazoles of formula I are prepared from reaction of a trisubstituted β-acylvinylphosphonium halide, preferably bromide or chloride, of the formula

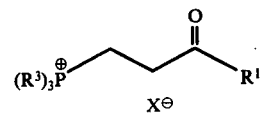

where $R^1$, $R^3$ and X are defined as above with a thiourea according to the procedure described by Zbiral, *Synthesis* 11:775 (1974) and Zbiral and Hugl, *Phosphorus* 2:29 (1972). Of course, one of the thiourea nitrogen atoms may be protected if desired during reaction with a β-acylvinylphosphonium halide with an easily removable monovalent amine protective group known to the art which is then removed to give the 2-aminothiazoles of formula II.

To prepare the trisubstituted β-acylvinylphosphonium halides not known to the art, a halovinyl alkyl ketone such as chlorovinyl methyl ketone is treated with a trialkyl- or triphenylphosphine. When $R^1$ is hydrogen the trisubstituted β-formylvinylphosphonium halides are prepared by oxidation of a β-haloallyl alcohol such as β-chloroallyl alcohol and treatment of the product thus formed with a trialkyl- or triphenylphosphine.

The process of this invention provides an inexpensive, efficient and high yield method for preparing certain thiazoles useful as intermediates in the preparation of pharmacologically active compounds. A further advantage of this process for the conversion of compounds of formula I to those of formula II is that the trisubstituted phosphines, $P(R^3)_3$, formed during the course of the reaction may be easily removed from the reaction mixture and recycled or otherwise reused.

The thiazole compounds of formula II prepared by the process of this invention are useful as intermediates for the production of pharmacologically active compounds, in particular histamine $H_2$-antagonists, for example N-cyano-N'-methyl-N''-[2-(4-$R^1$-thiazolylmethylthio)ethyl]guanidine and N-methyl-N'-[2-(4-$R^1$-thiazolylmethylthio)-ethyl]compounds. Histamine $H_2$-antagonists act at histamine $H_2$-receptors which as described by Black et al. [*Nature* 236:385 (1972)] may be defined as those histamine receptors which are not blocked by "antihistamines" such as mepyramine but are blocked by burimamide. Blockade of histamine $H_2$-receptors is of utility in inhibiting the biological actions of histamine which are not inhibited by "antihistamines". Histamine $H_2$-antagonists are useful, for example, as inhibitors of gastric acid secretion.

Conversion of the compounds of formula II to the pharmacologically active guanidine and thiourea products is accomplished in a variety of ways. When $R^2$ is $-SCH_2CH_2NH_2$, the 2-amino group of the 2-amino-5-(2-aminoethyl)thiomethylthiazole is removed, for example by reaction with ethylnitrite, to give the corresponding 5-(2-aminoethyl)thiomethylthiazole compound which is then treated with methyl isothiocyanate to give the corresponding N-methyl-N'-[2-(4-$R^1$-thiazolylmethylthio)ethyl]thioureas. Reaction of the same 5-(2-aminoethyl)thiomethylthiazole compound with N-cyano-N',S-dimethylisothiourea gives the corresponding N-cyano-N'-methyl-N''-[2-(4-$R^1$-thiazolylmethylthio)ethyl]guanidines. The guanidine products are also prepared by reaction of the 5-(2-aminoethyl)thiomethylthiazole with dimethyl-N-cyanoimidodithiocarbonate and subsequently reacting the resulting N-cyano-N'-[2-(4-R$^1$-thiazolylmethylthio)ethyl]-S-methylisothiourea with methylamine.

When the 2-amino group is desired as a substituent on the final product, the 2-amino-5-(2-aminoethyl)thiomethylthiazoles may be directly converted to the thioureas and guanidines as previously described.

When R$^2$ is methoxy, ethoxy, n-propoxy, n-butoxy, i-butoxy or t-butoxy, the 2-amino group of the compounds of formula II is removed as described above and the product thus formed is treated with cysteamine to give the 5-(2-aminoethyl)thiomethylthiazole compounds which are then converted to the guanidine and thiourea products as previously described. Alternatively, the 2-amino-5-alkoxymethylthiazoles may be treated with cysteamine to give the corresponding 2-amino-5-(2-aminoethyl)thiomethylthiazoles and the 2-amino group may be subsequently removed if desired as described above.

The thiourea and cyanoguanidine products prepared from the compounds of formula II are described in British Pat. No. 1,338,169.

The following examples illustrate the invention but are not intended to limit the scope thereof. Temperatures are in degrees Centigrade (° C.) unless otherwise indicated.

EXAMPLE 1

A solution of 41.1 g. (0.54 mole) of thiourea and 200 g. (0.54 mole) of triphenyl β-acetylvinylphosphonium chloride in 500 ml. of methanol was refluxed for 12 hours. The reaction mixture was evaporated to dryness to give a solid residue which was slurried with chloroform and collected by filtration to give [(2-amino-4-methylthiazolyl)-5-methyl]triphenylphosphonium chloride, m.p. 200°-205°.

[(2-Amino-4-methylthiazolyl)-5-methyl)]triphenylphosphonium chloride (60 g., 0.14 mole) was dissolved in 500 ml. of dry methanol and the solution was warmed to 55°-65°. Sodium methoxide solution (33 g. of 25% solution in methanol) was added with stirring and the mixture was heated at 55°-65° for 0.5 hour. After cooling to ambient temperature, the mixture was concentrated to one-third of the original volume, 150 ml. of water was added and the resulting suspension was acidified with hydrochloric acid. The mixture was filtered and the filtrate was extracted once with benzene. The aqueous phase was neutralized with dilute sodium hydroxide solution and extracted with chloroform. The extract was dried (MgSO$_4$) and evaporated to dryness to give 2-amino-5-methoxymethyl-4-methylthiazole, m.p. 132°-135° (ethyl acetate).

EXAMPLE 2

A solution of 4.17 g (0.01 mole) of [(2-amino-4-methylthiazolyl)-5-methyl]triphenylphosphonium chloride in 35 ml. of methanol was added to a slurry of the sodium salt of cysteamine, prepared from 1.15 g. (0.01 mole) of cysteamine hydrochloride and 1.1 g. (0.02 mole) of sodium methoxide, in 25 ml. of methanol. The mixture was refluxed for 1 hour, then cooled and diluted to three times the volume with water. The triphenyl phosphine was removed by filtration and the filtrate was extracted with three 50 ml. portions of chloroform. The combined extracts were dried (MgSO$_4$) and evaporated to dryness to give 2-amino-5-(aminoethyl)thiomethyl-4-methylthiazole (80%).

EXAMPLE 3

When an equivalent amount of triphenyl β-ethylcarbonylvinylphosphonium bromide or triphenyl β-isopropylcarbonylvinylphosphonium bromide is allowed to react with thiourea as described in the procedure of Example 1, [(2-amino-4-ethylthiazolyl)-5-methyl]triphenylphosphonium bromide and [(2-amino-4-isopropylthiazolyl)-5-methyl]triphenylphosphonium bromide are prepared, respectively.

Reaction of [(2-amino-4-ethylthiazolyl)-5-methyl]-triphenylphosphonium bromide and [(2-amino-4-isopropylthiazolyl)-5-methyl]triphenylphosphonium bromide with cysteamine in the presence of sodium methoxide or sodium hydride as described above gives 2-amino-5-(2-aminoethyl)thiomethyl-4-ethylthiazole and 2-amino-5-(2-aminoethyl)thiomethyl-4-isopropylthiazole, respectively.

In a similar manner, the triphenylphosphonium group of [(2-amino-4-ethylthiazolyl)-5-methyl]triphenylphosphonium bromide and [(2-amino-4-isopropylthiazolyl)-5-methyl]triphenylphosphonium bromide is displaced by reaction with other nucleophiles by procedures described herein.

EXAMPLE 4

When [(2-amino-4-methylthiazolyl-5-methyl]-triphenylphosphonium bromide is allowed to react with sodium ethoxide in ethanol, sodium n-propoxide in n-propanol or sodium t-butoxide in t-butanol according to the procedure described in Example 1, the following thiazole compounds are obtained:
2-amino-5-ethoxymethyl-4-methylthiazole
2-amino-4-methyl-5-n-propoxymethylthiazole
2-amino-5-t-butoxymethyl-4-methylthiazole.

EXAMPLE 5

To a solution of 9.25 g. (0.1 mole) of β-chloroallyl alcohol in 100 ml. of benzene is added an equivalent amount of an aqueous solution of chromic acid-sulfuric acid (Jones reagent) and the mixture is stirred at ambient temperature for 1 hour. After filtering, the layers are separated and the organic phase is washed with water. Triphenyl phosphine (26.2 g., 0.1 mole) is added to the benzene solution and it is heated to reflux. The precipitate which forms upon cooling is collected by filtration and dried to give β-formylvinylphosphonium chloride.

When an equivalent amount of β-formylvinylphosphonium chloride is allowed to react with thiourea as described in the procedure of Example 2, (2-aminothiazolyl-5-methyl)triphenylphosphonium chloride is prepared.

Reaction of (2-aminothiazolyl-5-methyl)triphenylphosphonium chloride with cysteamine in the presence of sodium methoxide or sodium hydride as described hereinabove gives 2-amino-5-(2-aminoethyl)thiomethylthiazole.

In a similar manner, the triphenylphosphonium group of (2-aminothiazolyl-5-methyl)triphenylphosphonium chloride is displaced by reaction with other nucleophiles by procedures described herein.

EXAMPLE 6

Tri-n-butylphosphine (20.2 g., 0.1 mole) is added to a solution of 10.4 g. (0.1 mole) of chlorovinyl methyl ketone in 250 ml. of benzene and the mixture is refluxed for 1 hour. The mixture is cooled and the precipitated material is collected by filtration and dried to give tri-n-butyl β-acetylvinylphosphonium chloride.

Triethyl β-acetylvinylphosphonium chloride is prepared as described above by use of triethylphosphine in place of tri-n-butylphosphine.

Reaction of an equivalent amount of tri-n-butyl β-acetylvinylphosphonium chloride or triethyl β-acetylvinylphosphonium chloride with thiourea as described in the procedure of Example 1 gives [(2-amino-4-methylthiazolyl)-5-methyl]-tri-n-butylphosphonium chloride and [(2-amino-4-methylthiazolyl)-5-methyl]-triethylphosphonium chloride, respectively.

Reaction of [(2-amino-4-methylthiazolyl)-5-methyl]-tri-n-butylphosphonium chloride or [(2-amino-4-methylthiazolyl)-5-methyl]triethylphosphonium chloride with cysteamine in the presence of sodium methoxide or sodium hydride as described hereinabove gives 2-amino-5-(2-aminoethyl)thiomethyl-4-methylthiazole.

EXAMPLE 7

A solution of 3.2 g. of 2-amino-5-methoxymethyl-4-methylthiazole in 100 ml. of dry tetrahydrofuran was brought to reflux and a solution of 6 g. of ethylnitrite in 75 ml. of dry tetrahydrofuran was added dropwise to the refluxing solution. After refluxing an additional 5 hours, the mixture was cooled and evaporated to give an oil. The oil was extracted into hexane and the hexane solution was evaporated to dryness to give 5-methoxymethyl-4-methylthiazole.

5-Methoxymethyl-4-methylthiazole (1.5 g.) was dissolved in 3 ml. of isopropanol and the solution was mixed with a hot solution of 0.38 g. of hydrochloric acid in 10 ml. of isopropanol which, upon cooling, gave 5-methoxymethyl-4-methylthiazole hydrochloride, m.p. 150°–152°.

5-Methoxymethyl-4-methylthiazole hydrochloride (1.04 g.) and 0.66 g. of cysteamine hydrochoride in 5.5 ml. of acetic acid was refluxed for 24 hours. The mixture was concentrated and the residue was dissolved in water. The aqueous solution was neutralized with sodium hydroxide and extracted with chloroform. The extract was dried (MgSO₄) and evaporated to dryness to give 5-(2-aminoethyl)thiomethyl-4-methylthiazole.

5-(2-Aminoethyl)thiomethyl-4-methylthiazole is treated with a hydrochloric acid solution to give 5-(2-aminoethyl)thiomethyl-4-methylthiazole dihydrochloride.

Potassium carbonate (7.75 g.) is added to a solution of 15.6 g. of 5-(2-aminoethyl)thiomethyl-4-methylthiazole dihydrochloride in 120 ml. of water. The solution is maintained at ambient temperature for 15 minutes and 5.15 g. of methyl isothiocyanate is added. After refluxing for 1.5 hours, the solution is cooled and the product is collected by filtration to give N-methyl-N'-[2-(4-methyl-5-thiazolylmethylthio)ethyl]-thiourea.

EXAMPLE 8 a. A solution of 19.7 g. of 4-(2-aminoethyl)thiomethyl-4-methylthiazole and 11.2 g. of N-cyano-N', S-dimethylisothiourea in 500 ml. of acetonitrile is refluxed for 24 hours. The mixture is concentrated and the residue is chromatographed on a column of silica gel to give N-cyano-N'-methyl-N''-[2-(4-methyl-5-thiazolylmethylthio)ethyl]guanidine.

b. A solution of 27.1 g. of 4-(2-aminoethyl)thiomethyl-4-methylthiazole in ethanol is added slowly to a solution of 20.0 g. of dimethyl-N-cyanoimidodithiocarbonate in ethanol, with stirring at ambient temperature. Filtration affords N-cyano-N'-[2-(4-methyl-5-thiazolylmethylthio)ethyl]-S-methylisothiourea.

A solution of 75 ml. of 33% methylamine in ethanol is added to a solution of the N-cyano-N'-[2-(4-methyl-5-thiazolylmethylthio)ethyl]-S-methylisothiourea prepared above in 30 ml. of ethanol. The reaction mixture is set aside at ambient temperature for 2.5 hours, and the precipitate is collected to give N-cyano-N'-methyl-N''-[2-(4-methyl-5-thiazolylmethylthio)ethyl]guanidine.

What is claimed is:

1. A process for preparing a compound of the formula:

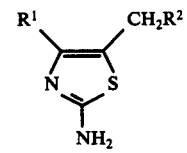

in which:

R¹ is hydrogen or lower alkyl; and
R² is methoxy, ethoxy, n-propoxy, n-butoxy, i-butoxy, t-butoxy or —SCH₂CH₂NH₂;

comprising reacting a compound of the formula:

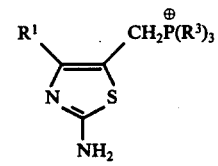

in which:

R¹ is defined as above;
R³ is lower alkyl or phenyl; and
X is halo, with a compound of the formula R²—H where R² is defined as above in an polar organic solvent and in the presence of a strong base.

2. A process according to claim 1 in which R³ is phenyl.

3. A process according to claim 2 in which R² is methoxy.

4. A process according to claim 2 in which R² is —SCH₂CH₂NH₂.

5. A process according to claim 3 for preparing 5-methoxymethyl-4-methylthiazole.

6. A process according to claim 4 for preparing 5-(2-aminoethyl)thiomethyl-4-methylthiazole.

7. A process according to claim 1 in which the base is sodium methoxide or sodium hydride.

8. A process according to claim 1 in which the solvent is methanol, ethanol, propanol, butanol, acetone, acetonitrile, dimethylformamide or dimethylsulfoxide.

9. A process according to claim 1 in which the reaction is carried out at a temperature of from about 25° to about 200° C. for from about 20 minutes to about 24 hours 10. A process according to claim 9 in which the reaction is carried out at a temperature of from about 50° to about 100° C. for from about 20 minutes to about 3 hours.

* * * * *

UNITED STATES PATENT AND TRADEMARK OFFICE
CERTIFICATE OF CORRECTION

PATENT NO. : 4,049,669
DATED : September 20, 1977
INVENTOR(S) : Bing Lun Lam, Joseph James Lewis
Robert Lee Webb, and George Robert Wellman It is certified that error appears in the above-identified patent and that said Letters Patent are hereby corrected as shown below:

Claim 1, the second structure should appear as:

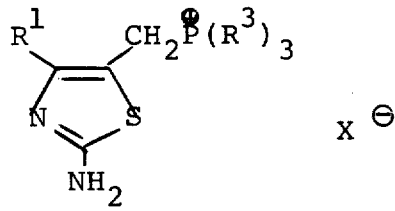

Claims 5 and 6 should read as follows:

5. A process according to claim 3 for preparing 2-amino-5-methoxymethyl-4-methylthiazole.

6. A process according to claim 4 for preparing 2-amino-5-(2-aminoethyl)thiomethyl-4-methylthiazole.

Example 8, Col. 5, line 58, and Col. 5, line 65, "4-(2-aminoethyl)" should read "5-(2-aminoethyl)".

Signed and Sealed this

Thirty-first Day of January 1978

[SEAL]

Attest:

RUTH C. MASON
*Attesting Officer*

LUTRELLE F. PARKER
*Acting Commissioner of Patents and Trademarks*